US010328034B2

(12) United States Patent
Stefanelli et al.

(10) Patent No.: US 10,328,034 B2
(45) Date of Patent: Jun. 25, 2019

(54) POLYMERIC ADHESIVE MATRIX WITH SALIFIED CARBOXYLIC GROUPS FOR TRANSDERMAL USE

(71) Applicant: BOUTY S.P.A., Milan (IT)

(72) Inventors: Paola Stefanelli, Milan (IT); Alberto Scarsetto, Cinisello Balsamo (IT); Maurizio Di Grigoli, Veduggio con Colzano (IT); Pierbruno Romelli, Rho (IT)

(73) Assignee: BOUTY S.P.A., Milan (IT)

( * ) Notice: Subject to any disclaimer, the term of this patent is extended or adjusted under 35 U.S.C. 154(b) by 0 days.

(21) Appl. No.: 15/414,829

(22) Filed: Jan. 25, 2017

(65) Prior Publication Data

US 2017/0128383 A1 May 11, 2017

Related U.S. Application Data

(63) Continuation of application No. 14/085,334, filed on Nov. 20, 2013, now abandoned, which is a continuation of application No. 11/659,379, filed as application No. PCT/EP2005/007293 on Jul. 6, 2005, now abandoned.

(30) Foreign Application Priority Data

Aug. 6, 2004 (IT) .............................. MI2004A1628

(51) Int. Cl.
| | |
|---|---|
| *A61K 9/70* | (2006.01) |
| *A61K 31/00* | (2006.01) |
| *A61K 31/192* | (2006.01) |
| *A61K 47/18* | (2017.01) |
| *A61K 47/32* | (2006.01) |
| *A61K 31/196* | (2006.01) |
| *A61K 47/59* | (2017.01) |

(52) U.S. Cl.
CPC .......... *A61K 9/7061* (2013.01); *A61K 9/7092* (2013.01); *A61K 31/00* (2013.01); *A61K 31/192* (2013.01); *A61K 31/196* (2013.01); *A61K 47/183* (2013.01); *A61K 47/32* (2013.01); *A61K 47/593* (2017.08)

(58) Field of Classification Search
CPC .... A61K 9/7061; A61K 31/00; A61K 31/192; A61K 47/183; A61K 47/32; A61K 9/7092; A61K 31/196; A61K 47/593
See application file for complete search history.

(56) References Cited

U.S. PATENT DOCUMENTS

| | | | |
|---|---|---|---|
| 4,540,572 A | 9/1985 | Seth | |
| 5,077,055 A * | 12/1991 | Muller | ................. A61K 9/7061 424/448 |
| 5,296,512 A | 3/1994 | Beier et al. | |
| 6,689,379 B1 * | 2/2004 | Bracht | .................... A61L 15/58 424/448 |
| 2001/0038861 A1 | 11/2001 | Hsu et al. | |
| 2002/0058068 A1 * | 5/2002 | Houze | ................. A61K 8/0208 424/487 |
| 2003/0129220 A1 | 7/2003 | Luo et al. | |
| 2004/0010054 A1 | 1/2004 | Koch et al. | |

FOREIGN PATENT DOCUMENTS

| | | | |
|---|---|---|---|
| CA | 2189970 A1 | 11/1995 | |
| CA | 2197866 A1 * | 2/1996 | ........... A61K 9/7007 |
| DE | 4429791 A1 | 2/1996 | |
| EP | 0394956 A1 | 10/1990 | |
| FR | 279770 | 11/1994 | |
| JP | 58103317 A | 6/1983 | |
| WO | 2003086370 A1 | 10/2003 | |

OTHER PUBLICATIONS

Eudragit E 100 Technical Data Sheet (Published by Evonik Industries and downloaded on Nov. 14, 2011).

* cited by examiner

*Primary Examiner* — Sean M Basquill
(74) *Attorney, Agent, or Firm* — Silvia Salvadori, P.C.; Silvia Salvadori

(57) ABSTRACT

Polymeric matrices for the controlled release of medicaments for the topical transdermal use comprising copolymers of acrylic and/or methacrylic acid or esters thereof having a Tg lower than 0° C., whose free carboxy groups are salified with compatible organic or inorganic bases. The matrices of the invention allow to prepare therapeutical systems for the controlled-release of active principles through the transdermal route, thus solving stability, solubility and/or bioavailability problems of the active ingredient within the matrix.

7 Claims, No Drawings

POLYMERIC ADHESIVE MATRIX WITH SALIFIED CARBOXYLIC GROUPS FOR TRANSDERMAL USE

This Application is a continuation of U.S. application Ser. No. 14/085,334 filed on Nov. 20, 2013, which is a continuation of U.S. application Ser. No. 11/659,379 filed on Aug. 4, 2008, which is a U.S. National Stage of PCT PCT/EP2005/007293 filed Jul. 6, 2005, which claims priority to and the benefit from Italian Patent Application MI2004A001628, filed Aug. 6, 2004, the contents of which are all incorporated herein by reference in their entireties.

The present invention relates to a polymeric matrix for the controlled-release of medicaments for the topical transdermal use, which matrix improves the solubility and the stability of the active ingredient.

TECHNOLOGICAL BACKGROUND

Controlled-release therapeutical systems (based on a matrix) for the transdermal administration are prepared by incorporation of an active ingredient (active principle) in a polymeric matrix, which acts both as adhesive and "container" for the medicament.

For this reason, a polymeric matrix must satisfy a series of specific requirements:
 ability to dissolve the active principle at the desired concentrations;
 absence of chemical interactions with the active principle, so as to avoid degradation or alteration;
 ability to allow the diffusion of the active principle towards the corneous layer;
 absence of irritation or erythema at the application site;
 ability to ensure adhesion of the system to the skin during the whole treatment period.

The matrices are made from solutions of adhesive polymers also referred to as "pressure sensitive adhesives".

The most commonly used polymers are of acrylic type and are commercially available in the form of powders, granules, aqueous or solvent solutions.

In general, the polymers used for pharmaceutical formulations belong to two classes, those with a glass transition temperature (Tg) higher than room temperature (or use temperature) and those with a Tg lower than room temperature. The former need plasticizers to be used in the formulation of transdermal patches, while the latter can be used as such, since they already have a soft consistency. For this reason, polymers with a Tg <room T are preferred, even if, due to their properties, they are commercialised dissolved in organic solvents.

Many of these polymers are copolymers of acrylic or methacrylic acid and/or esters thereof, therefore the polymer chains contain acidic functions which can interact with the active principle causing oxidation and/or degradation of the active principle.

It has now been found that matrix-based therapeutical systems for the controlled release of medicaments can be prepared by suitably salifying the free carboxy groups of the polymer chains of macromolecules mixtures having a lower Tg.

DISCLOSURE OF THE INVENTION

The invention relates to a polymeric matrix for the controlled release of medicaments for the topical transdermal use, which matrix comprises copolymers of acrylic or methacrylic acid and/or esters thereof having a Tg lower than 0° C. and wherein the free carboxy groups are salified with compatible organic or inorganic bases.

The copolymers that can be used according to the invention consist of two or more monomers in various percentages.

Examples of said monomers comprise:
 acrylic acid
 butyl acrylate
 2-ethylhexyl acrylate
 glycidyl methacrylate
 2-hydroxyethyl acrylate
 methyl acrylate
 vinyl acetate
 t-octylacrylamide Examples of copolymers according to the invention comprise poly(2-ethyl-hexyl acrylate-co-acrylic acid), poly(2-hydroxy-ethyl acrylate-co-acrylic acid-co-methyl-acrylates), poly(2-ethyl-hexyl acrylate-co-acrylic acid-co-methylacrylate), poly(2-ethyl-hexyl acrylate-co-acrylic acid-co-butilacrylate-co-vinyl acetate).

These copolymers are commercially available with the following trade names: Duro-tak® (National and Starch), MG-0607® (Dow Corning), Gelva® (UCB chemicals), Luvimer® (BASF).

These acrylic or methacrylic copolymers have a percentage of free carboxy groups of 0.1-15%, preferably 1-10%. Since they are not hot-extrudable, they are commercialised dissolved in organic solvents.

The bases with which the carboxy groups are salified can be either inorganic, for example alkali, alkaline-earth or transition metals hydroxides, carbonates or bicarbonates, or organic, for example ammonia, ammonium methyl acrylates copolymers, ethylenediamine, lysine.

The matrices of the invention further comprise from 0.1 to 20% by weight of water, preferably 1 to 5%.

The invention allows to formulate any active ingredient having therapeutical, dermatological or cosmetic activity when administered through topical and/or transdermal route.

Examples of medicaments which can be advantageously formulated according to the invention comprise: non steroidal antiinflammatory agents, corticosteroids, local anaesthetics, alpha-adrenergic agonists, analgesics, antimigraine drugs, anti-allergics, antihistaminics, antimicrobials, antiemetics, anticholinergics, bronchodilators, antivirals, myorelaxants, cholinergic agents, central nervous system stimulators, cardioactive agents, beta-adrenergic agonists, hormones, anxiolytics, antidepressants, antipsychotics, opioid antagonists, coronary dilators.

Particularly preferred are non steroidal antiinflammatories such as Diclofenac, Fenoprofen, Flurbiprofen, Ibuprofen, Ibuproxam, Indoprofen, Ketoprofen, Ketorolac, Naproxen, Oxametacine, Oxyphenbutazone, Piroxicam, Suprofen, Celecoxib and other COX-2 selective inhibitors and the like.

The matrices of the invention are particularly suitable as adhesive layers in transdermal patches.

A further object of the invention is a process for the preparation of transdermal matrices which comprises the treatment of a copolymer having a Tg lower than 0° C. and free carboxy groups suspended in an organic solvent with an aqueous solution of organic or inorganic bases in stoichiometric amounts in respect of the carboxylic groups, followed by addition of the active ingredient and any other excipients.

The matrices of the invention allow to improve the solubility, the stability and the diffusion of the active principle from the matrix.

DETAILED DISCLOSURE OF THE INVENTION

The polymeric matrix in the final formulation can be present in an amount ranging from 20 to 95%, preferably from 50 to 90%, based on the dry weight of the final composition.

The acidic groups are neutralized with stoichiometric amounts of inorganic (alkali and transition metal hydroxides, e.g. sodium hydroxide, potassium hydroxide) or organic (e.g. ammonia, ammonium methyl acrylate copolymers, ethylenediamine, lysine) bases in the presence of a suitable amount of demineralised water to promote ion-exchange between the acidic groups of the polymeric structure and the basic counter-ion in a solvent system.

Water is used in an amount that forms the solvatation sphere of the free ions without destabilizing the solvent system, so as to prevent precipitation of the polymer. The polymeric matrix, at first solvent-based, is transformed according to the invention into a solvent/water-based mixture. The amount of water ranges from 0.1 to 20%, preferably from 1 to 5% based on the wet weight of the adhesive mixture.

In this way the acidic functions are neutralised and interactions with the active principle are avoided.

The active principle dissolves completely at high concentrations in this system through synergistic interaction of the polymeric matrix, the solvent and the ion exchanges promoted by water protons. The amount of active principle incorporated in the system varies according to the nature of the active principle and the desired therapeutical effect.

Usually, the amount of active principle ranges from 0.1 to 50%, preferably from 0.1 to 30% based on the dry weight of the final composition. After drying, the polymeric matrix that contains the active principle forms a controlled-release therapeutical system for the topical use. This matrix promotes the diffusion of the active principle, as the salification of the acidic groups in the polymeric chains makes the matrix structure more hydrophilic.

The formulation can contain one or more excipients having different functions, for example skin-emollients, percutaneous permeation enhancers, preservatives and the like. The amount of each excipient varies within broad ranges, for example from 0.01 to 30%, and according to their action. Preservatives are usually comprised in the final formulation in amounts of 0.01-2%, whereas emollients are comprised in the final formulation in amounts of 5-20%.

The invention is illustrated in greater detail in the following examples.

Example 1

1 kg of Durotak® 87-2852 (poly(2-ethyl hexyl acrylate-co-acrylic acid-co-methyl acrylate)), having a solid content of 33.5% w/w, is added under mechanical stirring with 62 g of a 32% w/w potassium hydroxide aqueous solution; the mixture becomes more viscous and is left under moderate stirring for 30 min.

Thereafter, 90 g of Diclofenac are added, and stirring is continued until complete dissolution.

For the preparation of the matrix layer, the mixture is spread on a film of silicon polyester and the solvents are evaporated off in a static drier, heating at 60° C. for 20 min. The spread matrix has a dry weight of about 50 g/m$^2$. After coupling to a polyethylene film, the patch is formed with a suitable punch.

Example 2

1 kg of Durotak® 87-2051 (poly(2-ethyl-hexyl acrylate-co-acrylic acid-co-butyl acrylate-co-vinyl acetate)), having a solid content of 51% w/w, is added under mechanical stirring with 64 g of a 32% w/w potassium hydroxide aqueous solution; the mixture becomes more viscous and is left under moderate stirring for 30 min.

Thereafter, 90 g of Ketoprofen are added, and stirring is continued until complete dissolution.

For the preparation of the matrix layer, the mixture is spread on a film of silicon polyester and the solvents are evaporated off in a static drier, heating at 60° C. for 20 min. The spread matrix has a dry weight of about 60 g/m$^2$. After coupling to a polyethylene film, the patch is formed with a suitable punch.

Example 3

1 kg of Durotak® 87-2852, having a content solid of 33.5% w/w, is added under mechanical stirring with 300 g of a 30% w/w Eudragit E100 water/solvent-based solution; the mixture becomes more viscous and is left under moderate stirring for 30 min.

Thereafter, 100 g of Diclofenac are added, and stirring is continued until complete dissolution.

For the preparation of the matrix layer, the mixture is spread on a film of silicon polyester and the solvents are evaporated off in a static drier, heating at 60° C. for 20 min. The spread matrix has a dry weight of about 60 g/m$^2$. After coupling to a polyethylene film, the patch is formed with a suitable punch.

The invention claimed is:

1. Topical transdermal controlled release systems of medicaments consisting of:
   diclofenac as medicament;
   a polymeric matrix for said controlled release of said medicaments, said polymeric matrix consisting of copolymers of poly(2-ethyl-hexyl acrylate-co-acrylic acid-co-methyl acrylates) having a Tg lower than 0° C., wherein the free carboxylic groups are salified with stoichiometric amounts of amino methyl-acrylate copolymers.

2. The system as claimed in claim 1, wherein the poly(2-ethyl-hexyl acrylate-co-acrylic acid-co-methyl acrylates) copolymers have a percentage of free carboxy groups ranging from 0.1 to 15%.

3. The system as claimed in claim 2 wherein the poly(2-ethyl-hexyl acrylate-co-acrylic acid-co-methyl acrylates) copolymers have a percentage of free carboxy groups ranging from 1 to 10%.

4. Topical transdermal controlled release systems of medicaments consisting of:
   diclofenac as medicament;
   0.1 to 20% by weight of water, and
   a polymeric matrix for said controlled release of said medicaments, said polymeric matrix consisting of copolymers of poly(2-ethyl-hexyl acrylate-co-acrylic acid-co-methyl acrylates) having a Tg lower than 0° C., wherein the free carboxylic groups are salified with stoichiometric amounts of amino methyl-acrylate copolymers.

5. The system as claimed in claim 4, wherein water is present in an amount of between 1 to 5% by weight.

6. A transdermal patch comprising as an adhesive layer a composition according to claim 1.

7. A process for the preparation of a topical transdermal controlled release systems of medicaments which comprises the treatment-of the copolymer of claim 1 having a Tg lower than 0° C. and free carboxy groups suspended in an organic solvent with an aqueous solution of amino methyl acrylate copolymers in stoichiometric amounts with respect to the carboxylic groups, followed by addition of an active ingredient and any other excipients, wherein said active ingredient is diclofenac.

* * * * *